United States Patent [19]

Nowak

[11] Patent Number: 4,879,652
[45] Date of Patent: Nov. 7, 1989

[54] METHOD FOR PRODUCING THREE-DIMENSIONAL IMAGES FROM NUCLEAR DATA

[75] Inventor: David J. Nowak, Greendale, Wis.

[73] Assignee: General Electric Company, Milwaukee, Wis.

[21] Appl. No.: 93,437

[22] Filed: Sep. 4, 1987

[51] Int. Cl.[4] ............................................. G06F 15/42
[52] U.S. Cl. ........................... 364/413.18; 364/413.24
[58] Field of Search ........... 364/414, 522, 723, 413.18, 364/413.24; 340/729, 728

[56] References Cited

U.S. PATENT DOCUMENTS

| | | | |
|---|---|---|---|
| T912,012 | 7/1973 | Appel et al. | 340/729 |
| 3,919,556 | 11/1975 | Berninger | 250/366 |
| 4,497,024 | 1/1985 | Roth | 364/414 |
| 4,580,219 | 4/1986 | Pelc et al. | 364/414 |
| 4,709,231 | 11/1987 | Sakaibara et al. | 364/522 |
| 4,737,921 | 4/1988 | Goldwasser et al. | 364/522 |
| 4,766,556 | 8/1988 | Arakawa | 364/522 |

OTHER PUBLICATIONS

Kouris et al., "Reconstruction from Sparsely Sampled Data by ART with Interpolated Rays" *IEEE Transactions on Medical Imaging* vol. MI-1, No. 3, Nov. 1982, pp. 161–167.

"Implementation of Three-Dimensional Display Algorithms For the Display of Three-Dimensional Computerized Tomographic Images On A Large Minicomputer" Enrique Santos, Thesis Submitted to Marquette University, Milwaukee, Wis., Jul. 1986.

"Medical Imaging Systems", Albert Macovski, Prentice-Hall, Inc., pp. 145–151, 166–167; undated.

*Primary Examiner*—Jerry Smith
*Assistant Examiner*—David M. Huntley
*Attorney, Agent, or Firm*—Quarles & Brady

[57] ABSTRACT

A nuclear imaging tomographic scanner acquires data from a volume of interest and a tomographic reconstruction is used to produce a three-dimensional array of data elements. A three-dimensional image of an object within this volume of interest as viewed from a projection plane is created using this three-dimensional array of data. The resulting two-dimensional data is shaded by determining the distance between the projection plane and points on the surface of the object. The exact distance is determined using an interpolation method and more distant points are shaded darker. The shading is further accentuated by measuring the gradient of the object's surface and shading points on the surface with a higher gradient darker.

6 Claims, 5 Drawing Sheets

METHOD FOR PRODUCING THREE-DIMENSIONAL IMAGES FROM NUCLEAR DATA

BACKGROUND OF THE INVENTION

The field of the invention is image display systems for nuclear or gamma cameras such as are used in the practice of nuclear medicine.

Nuclear imaging tomographic scanners such as those described in U.S. Pat. Nos. 4,652,758 and 4,497,024 include a sensor, or camera, which is sensitive to emissions from radioactive substances within the patient. The camera is typically moved around the patient and data is obtained from many angles. From the resulting data set a two-dimensional image can be reconstructed using well known computer tomographic (CT) techniques. Such two-dimensional images are cross sectional views through the patient and to obtain three-dimensional information from the data set, a series of spaced cross sectional views are reconstructed and the radiologist examines them all to reconstruct in his mind the three-dimensional image.

Three dimensional shaded surface images provide the radiologist with unique views of the radiopharmaceutical distributions within the patient. There are many known methods for producing such images from data sets collected using x-ray computerized tomography technology, nuclear magnetic resonance technology and nuclear imaging technology. These methods all require considerable computation time, and in the case of nuclear imaging technology, the images have not been particularly good because of the limited amount of data which is collected during a typical scan. This limitation on data translates into relatively low resolution 2-D images and inaccurate 3-D images.

The reconstruction of a 3-D shaded surface image may be accomplished in a number of well known ways. The first step is to extract from the data acquired throughout the scanned volume the data pertaining to the surface of the object of interest. This is usually accomplished either manually, or by a technique called thresholding. The thresholding technique identifies all those data points in the scanned volume where the nuclear events have exceeded a preset threshold value. Data points with lower numbers of events are considered background and the boundary between the background data points and the data points within the object of interest is the surface which is to be imaged.

After an object is identified, a mathmatical representation of the surface of the object is created using techniques such as the cuberille algorithm, contour-based algorithms, the octree-encoding algorithm or the ray-tracing algorithm. Surface display techniques are then employed to synthesize a 3-D image of the object. Such surface display techniques include hidden-surface removal, shading, translation, projection, scaling and rotation of the object of interest.

The ray-tracing method of creating a 3-D surface is particularly attractive since a separate pre-processing step is not required. With the so-called Vannier's method, for example, a projection plane perpendicular to the cross-sections of the object data set is established. Projectors perpendicular to the projection plane are traced toward the scanned volume. As a projector intersects a data point, or voxel, a thresholding test is applied to determine if that point is located on the surface of the object of interest. If the number of nuclear events exceeds the threshold value at the point, a point of the surface has been located and the projector stops. A shading value then assigned to the pixel in the plane from which the projector eminated. If the projection does not intersect the object of interest, its pixel shading value is set to the background value.

While the ray-tracing methods are particularly attractive with data acquired using x-ray computer tomography, the quality of the images has been less than satisfactory when such methods are applied to data sets acquired with nuclear imaging tomographic scanners. The primary reason for this is that fewer data points are acquired for a given volume of interest and reconstructed images have "staircase" artifacts.

SUMMARY OF THE INVENTION

The present invention is an improved method for reconstructing three-dimensional surface images from data acquired using a nuclear imaging tomographic scanner. The method includes producing a three-dimensional array of data points which represent the number of nuclear events in a volume of interest, incrementally extending a projector from each pixel in a projection plane into the volume of interest, detecting the point where each projector directed at an object of interest has reached data points which exceed a pre-established threshold value, locating the point at which each such projector intersects the object of interest by interpolating between the current value of the data points and the value of the data points at the previous increment, assigning a shading value to the pixel in the projection plane from which each intersecting projector eminates, this shading value being calculated as a function of the length of the intersecting projector. Yet another aspect of the invention is to add an additional shading value to each pixel which is a function of the gradient of the object's surface at the point where the pixel's projector intersects. The gradient is calculated using a 2 × 2 convolution operator.

A general object of the invention is to improve the quality of three-dimensional surface images. By calculating the value of additional data points from the acquired data set, the granularity of the image is reduced along one coordinate. By calculating the value of adjacent data points surrounding each advancing projector, and by locating more precisely the intersection of each projector with the object's surface, the granularity of the image along the other two coordinates is reduced. The image quality is thus improved in all three-dimensions.

Yet another object of the invention is to improve image quality without unduly increasing processing time. By locating the exact intersection point of each projector using an interpolation technique a more accurate depth indication can be produced on the three-dimensional image. This increased accuracy is achieved without shortening the incremental distance the projector is advanced with the consequent increase in processing time.

These and other objects and advantages of the invention will appear from the following description. In the description, reference is made to the accompanying drawings which form a part hereof, and in which there is shown a preferred embodiment of the invention. Such embodiment does not necessarily represent the full scope of the invention, and reference is made, therefore,

DESCRIPTION OF THE PREFERRED EMBODIMENT

Figure 1:
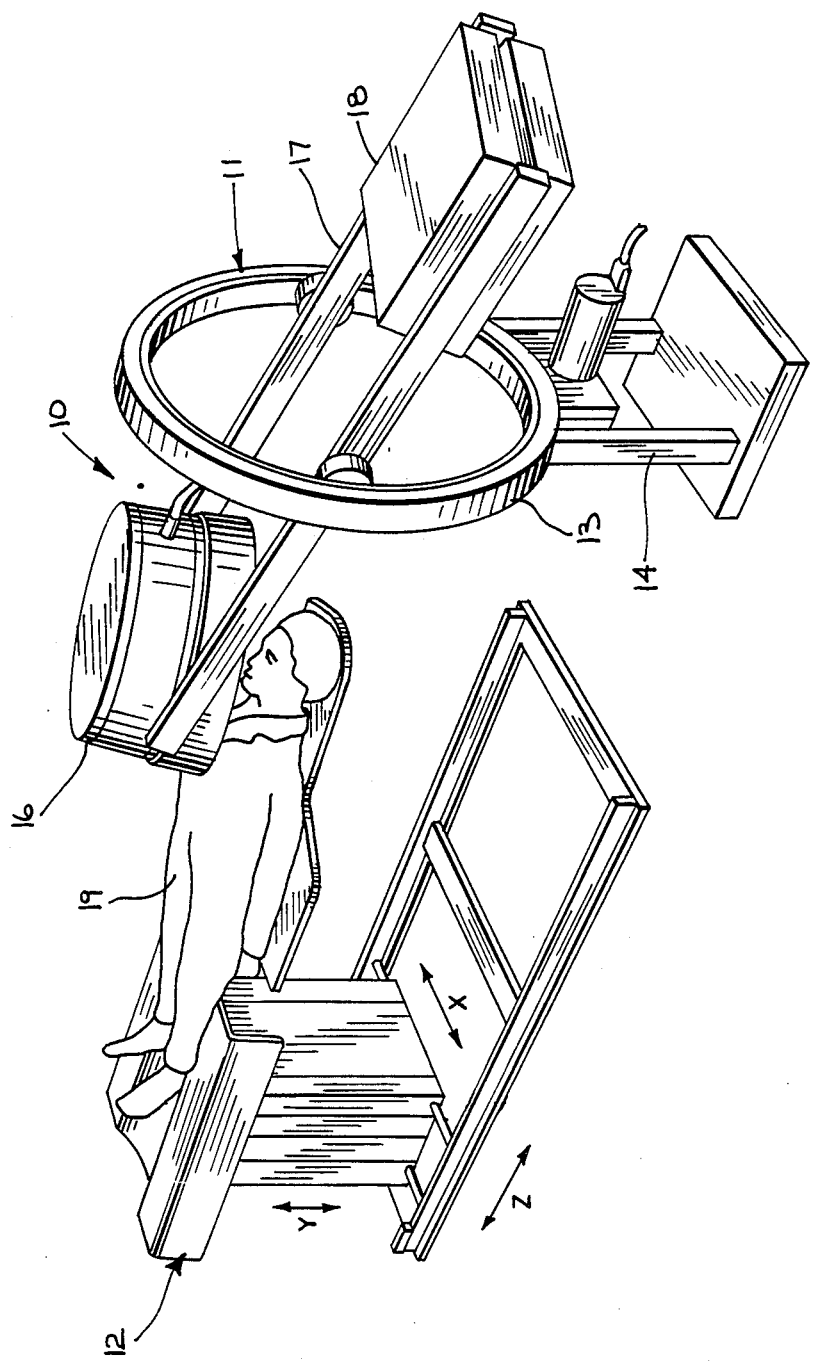
FIG. 1 is a pictoral view of nuclear imaging tomographic scanner which employs the present invention.

Referring to FIG. 1, there is shown, generally at 10, a nuclear imaging tomograpic scanning system which includes a tomographic scanner 11, and a patient support table 12. The construction and operation of the scanner 11 is similar to that shown and described in U.S. Pat. No. 4,216,381, issued on Aug. 5, 1980, and assigned to the assignee of the present invention. Briefly, the scanner 11 comprises an annular gantry 13 supported in a vertical position as shown by a pedestal 14 and having a camera head 16 supported from the gantry 13 in cantilevered fashion by an arm assembly 17 and balanced by a counterweight 18 on the other end of the arm assembly 17. The arm assembly 17 is so connected to the gantry 13 as to allow the entire arm assembly 17 to be rotated within the gantry 13 by a motor-drive system (not shown), to thereby rotate the camera head 16 in a circular path around the patient 19 supported on the table 12 for the purpose of gathering data which can be used to reconstruct a tomographic image of the patient in the area of concern. The structure and operational movement of the scanner 11 is of a conventional nature.

Figure 2:
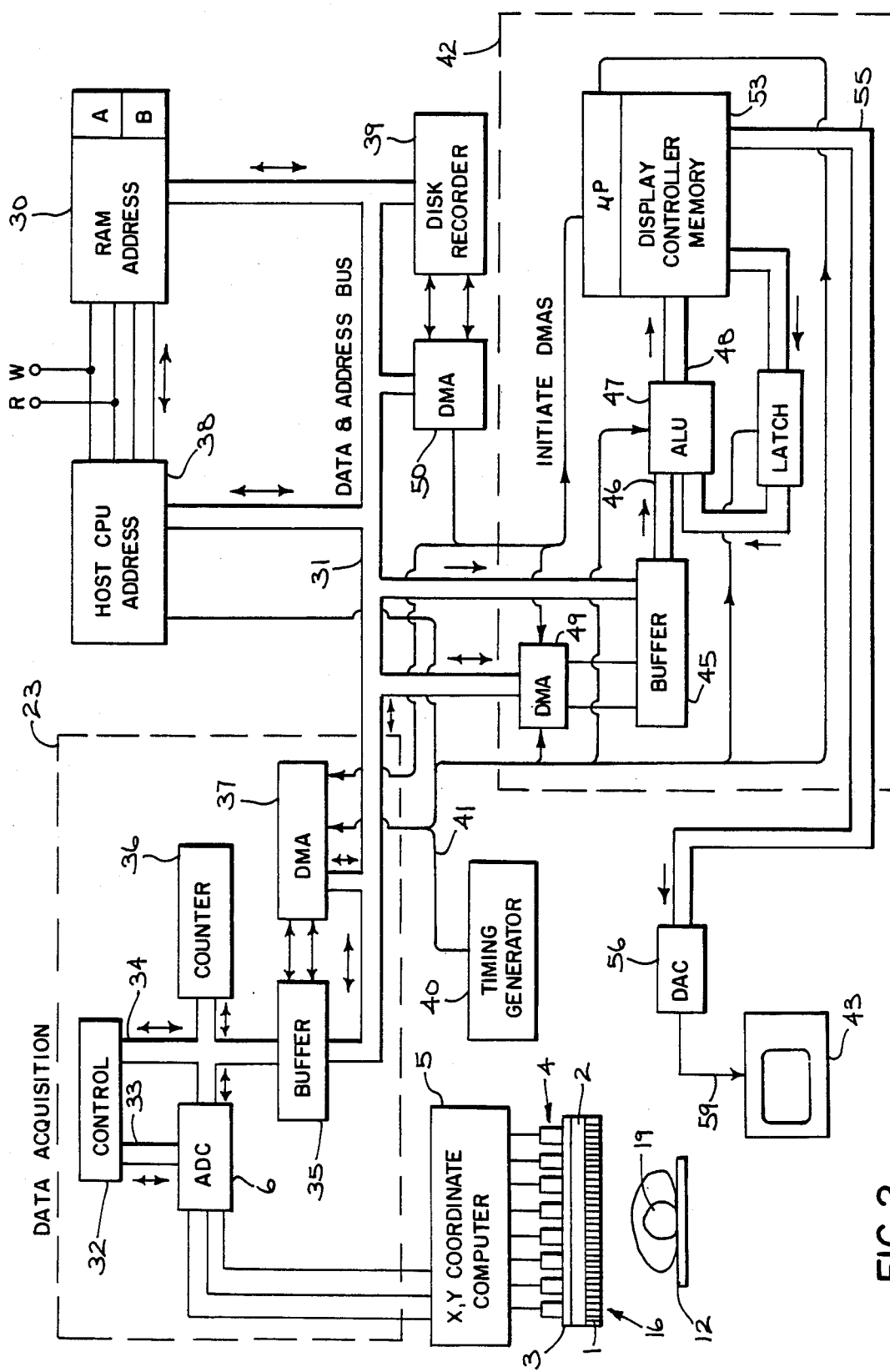
FIG. 2 is an electrical block diagram of the control system for the scanner of FIG. 1.

Referring to FIG. 2, as is well known, the various isotopes used in nuclear medicine emit gamma ray photons in a pattern which permits visualizing the configuration of body tissue and blood vessels. The nuclear or gamma camera 16 used to detect and identify the coordinates of the gamma ray photon emissions is conventional. The camera comprises a lead plate 1 that has a myriad of fine holes so that the plate acts as a collimator. Interfaced with the collimator is a scintillation crystal 2 which produces scintillations wherever photons are absorbed by it. The scintillations are coupled by means of a glass plate 3 to an array of photomultiplier tubes which are collectively designated by the numeral 4. The photomultiplier tubes are usually packed closely with each other within a circle as is well known. Any detected scintillation causes the photomultiplier tubes 4 to produce respective analog signals which are sent to a computer that is symbolized by the block marked 5. The computer 5 uses the signals to compute the x and y coordinates of each scintillation event in terms of analog signal magnitudes. Computing the x and y coordinates in terms of analog signals is well known. One scheme for determining the x and y coordinates of each scintillation is described in U.S. Pat. No. 4,142,102. The analog x and y coordinate signals are transmitted from the computer 5 to an analog-to-digital converter (ADC) represented by the block marked 6. A third line running from the computer 5 carries a signal, commonly called a z signal, which is indicative of whether the magnitude of the scintillation pulse was high enough or of the correct isotope to be considered a valid pulse.

ADC 6 is part of a data acquisition module which is within the boundaries of the dashed line 23. The output of ADC 6 to a bus 34 is a series of digital number pairs which correspond to the x and y coordinates, or the addresses, of the scintillations. Each scintillation falls within the boundaries of one of the pixels which define the image frame. The digital coordinate values are used as addresses to locations in a random access memory (RAM) that is generally designated by the numeral 30 and appears in the upper right portion of FIG. 2.

In the frame mode of operation, every time a pixel location in the memory 30 is addressed, the digital number representing the number of scintillation events at that pixel address is taken out of that location and incremented by one so that at the end of an exposure interval the number in the memory location is representative of the brightness or intensity of the pixel. The buses for transferring data and addresses are represented collectively by a single bus 31 on which the legend, "data and address bus" has been applied.

The data acquisition module 23 is involved in the memory location incrementing operation just described. It contains a control that is represented by the block marked 32. It is coupled to ADC 6 with a bidirectional control bus 33 and it also has a bus 34 which connects to the data and address bus 31 through a buffer 35. There is also an event counter 36 and a direct memory access (DMA) controller 37 in the acquisition module 23. The host central processor or computer for the system is represented by the block marked 38. The host central processor unit 38 will hereinafter be called the CPU for the sake of brevity.

As indicated above, every time a location in RAM 30 is to be incremented by 1, the present contents are withdrawn from the affected locations and sent to the control 32 where the digital value is incremented and then returned back to the memory location. The host CPU 38 provides the signals for causing DMA 37 to make the data transfers at the proper time from ADC 6 to RAM 30 and from the RAM 30 to data acquisition control unit 32 for incrementing. Buffer 35 is for the conventional purposes of interchanging data between buses or components in proper timing and for assuring that the data is stabilized before a transfer is made. Counter 36 in data acquisition module 23 is for counting the total number of scintillation events during a particular exposure of study.

For tomographic acquisitions, a set of two-dimensional images are acquired by the camera over a fixed time interval as it moves in its circular path about the patient. Each image is a frame of acquired data which is not only stored in the RAM 30, but also is stored in a disk recorder represented by the block marked 39 and a display controller which is represented by the dashed line block 42. Thus, all of the pixel intensity data for each frame is also available from disk recorder 39 at any time. To permit making a sequence of frames without requiring excessive memory capacity in RAM 30, the RAM memory is divided into sectors or blocks which are symbolized by those marked A and B in RAM 30. Thus, pixel data are acquired in a block of memory A for a predetermined time interval determined by CPU 38. After the end of that interval and before the block of memory is overloaded, the pixel data are transferred to disk recorder 39 and to the display controller 42 while at the same time the incoming data from the data acquisition module are switched to the other memory block B so there is no interruption in data acquisition. The acquisition data are repeatedly switched back and forth between blocks A and B in RAM 30 until the host CPU 38 brings about termination of the study. Thus, from the description so far, one may see that the pixel data for a frame currently being acquired is in one of the memory blocks A or B and also available, as required from disk recorder 39 and presented for display from the display controller 42. The digital numbers acquired in RAM 30, disk recorder 39, and display controller 42 in the frame mode have a value corresponding to the number of nuclear events which occur at points throughout the volume of interest.

A timing generator symbolized by the block marked 40 is provided for properly timing and synchronizing data and address transfer events in the system. Lines such as the one marked 41 leading out from the timing generator 40 are shown to indicate that the timing function is present.

The display controller 42, has a memory 53 for accepting the pixel or image frame data and bringing about display of the data as an image on the CRT which is represented by the block marked 43. When the data for a frame has been acquired, it is transferred by way of bus 80 through a buffer 45. The buffer is coupled by way of a bus 46 to an arithmetic logic unit (ALU) which is represented by the block marked 47. The output of ALU 47 is coupled, by means of a bus 48 to an input of display controller memory 563. ALU 47, besides having the capability for adding or subtracting digital pixel data before it enters the display controller, can also let the data from bus 46 flow through without operating on it as it goes to the display controller memory 63. A DMA 49 is used to control transfer of pixel data from RAM 30 through buffer 45 to ALU 47 at appropriate times. DMA 49 performs the traditional function of notifying the CPU 38 that the data bus 31 is required for making a transfer from RAM 30 to ALU 47 and display memory 53.

Another DMA 50 is associated with disk recorder 39 and its purpose is to transfer data in and out of disk recorder 39 at the proper times. DMA 50 can be used to control transfer of data from RAM memory 30 to the disk recorder 39 as mentioned above and it can also control transfer of data from disk recorder 39 to RAM 30 when one desires to display a sequence of images that are stored on disk.

Assume now that the pixel data for an image frame is now in the memory 53 of the display controller 42. Typically the display controller memory has a 64 × 64 or a 128 × 128 pixel array. The brightness or intensity of each pixel is represented by the value of a digital number in the respective display controller memory locations. The digital values must be converted to analog video signals for permitting display on CRT 43. Typically, the bit range of the display controller memory locations is 12-bits. The 12-bit digital values are transferred in sequence by way of a bus 55 to a digital-to-analog converter or, DAC 56, where the digital data is converted to analog video signals which are sent by means of a cable 59 to CRT 43 to effectuate display of the image.

Figure 3:
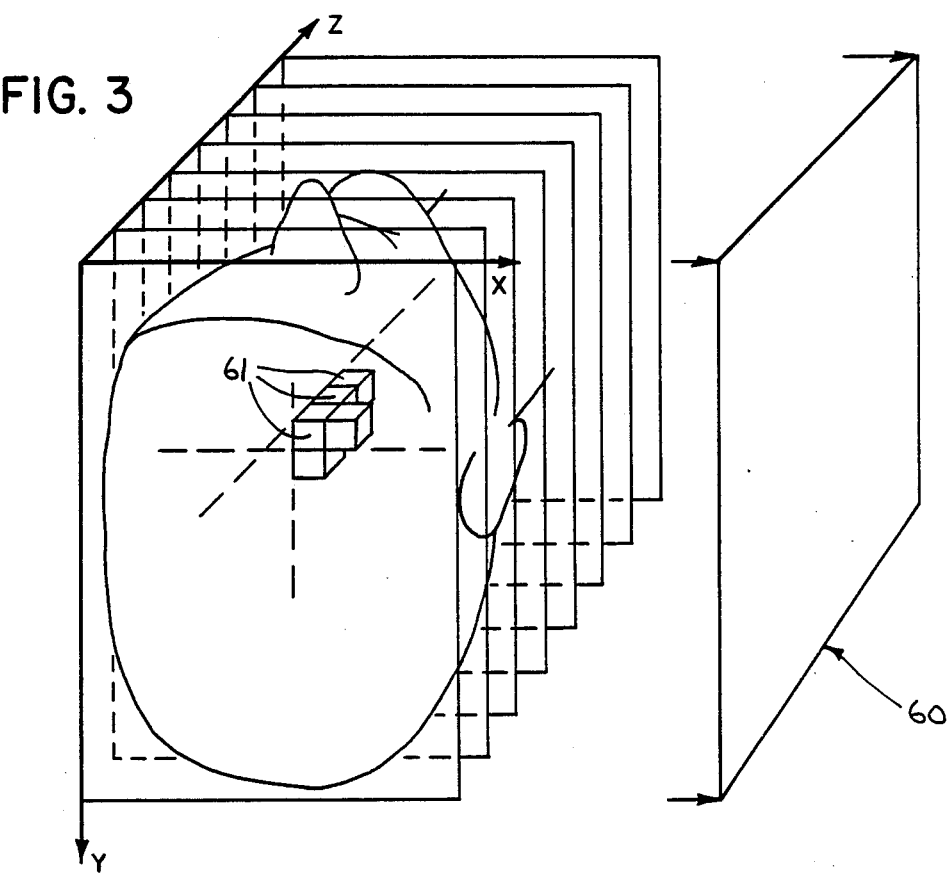
FIG. 3 is a graphic representation of the three-dimensional data set which is reconstructed from the data which is acquired by the scanner of FIG. 1.

At the completion of a scan of the patient the disk recorder 39 stores a data set for a plurality of frames. Each frame includes sufficient data to produce a two-dimensional image on the display 43 which represents the intensity of the scintillation events as seen from one of a plurality of the camera viewing planes disposed around the patient. Computer tomography is then employed to reconstruct from this acquired data the slices taken through the region of interest as shown in FIG. 3. The slices are parallel to each other and they are evenly spaced apart along the third dimension (Z axis). As is well known in the art, this data set can be transformed in the CPU 38 to reorient the slices along any axis such that a series of two-dimensional images taken through the patient at any point and at any angle can be reconstructed. The present invention is a method for transforming this stored three-dimensional data set into a three-dimensional picture which is projected onto a two-dimensional plane selected by the user. Such a plane is indicated at 60 in FIG. 3 and the picture which is reconstructed is shaded to show the three-dimensional contour of the subject. The calculations necessary to produce this 3-D image are carried out by the CPU 38 and the resulting frame of data is stored in the disk recorder 39 and output to the display controller 42.

Referring particularly to FIG. 3, the data set which is acquired during a complete scan of the patient is used to reconstruct a set of data points which indicate the number of nuclear events which have occurred at locations, or voxels 61, arranged in a three-dimensional matrix. In the preferred embodiment the region of interest contains 64 voxels along the x coordinate, 64 voxels along the y coordinate, 64 voxels along the z coordinate, for a total of 262,144 data points. The voxels are 6.4 millimeter cubes, and as indicated above, the data set is aranged as sixty-four slices, each containing 64×64=4096 data points.

Figure 4:
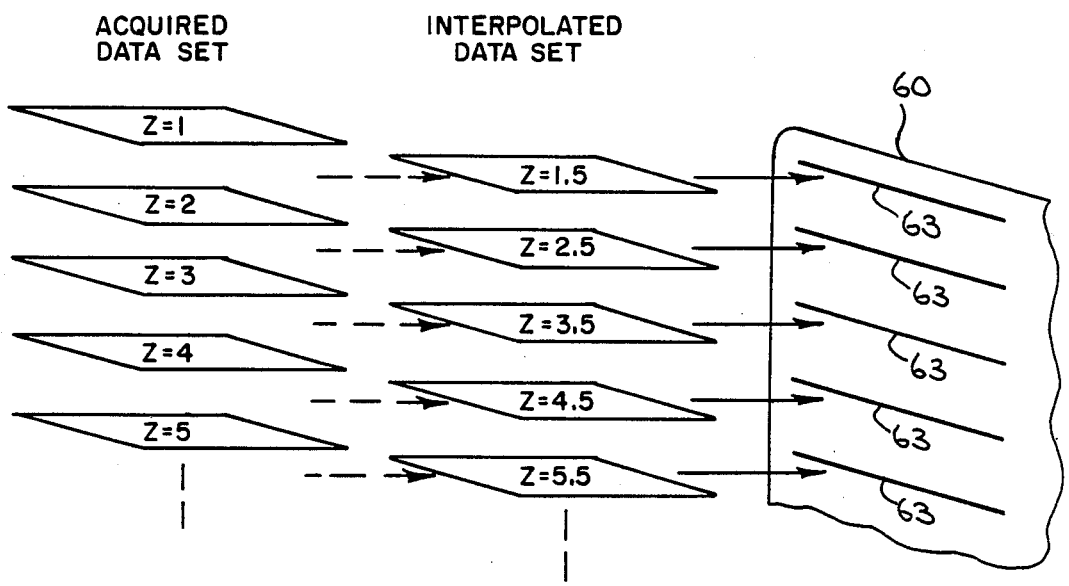
FIGS. 4 and 5 are pictoral representations of one step in the method of the present invention.
Figure 5:
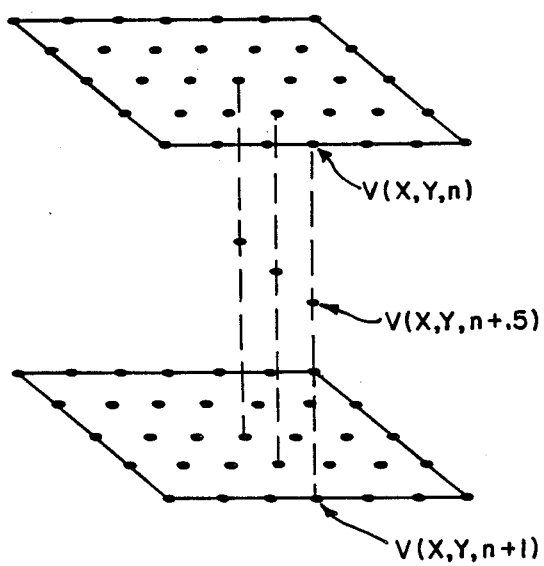

Referring to FIGS. 4 & 5, the first step in the present method is to calculate sixty-three new slices of data from the data set using a linear interpolation process. Each slice of reconstructed data represents the nuclear events in one slice ($z_n$) along the z axis which is spaced apart 6.4 millimeters from the adjacent slices ($z_{n-1}$ and $z_{n+1}$). The new slice set is formed by producing slices located midway between the slices of the reconstructed data set. The 4096 data points in each such calculated slice are determined by linearly interpolating between corresponding data points in the adjacent slices.

$$v(x,y,n+0.5)=(v(x,y,n)+v(x,y,n+1))/2 \qquad (1)$$

While this initial interpolation step is not necessary to practice the remainder of the invented method, it has been discovered that this initial step does significantly improve image quality. The interpolation in the direction of slice position (i.e. z coordinate) has been found to smooth the acquired data along that coordinate and to significantly reduce "staircase" artifacts which often plague nuclear images. As will be described below, subsequent steps in the method perform similar smoothing functions on the data along the other two coordinates to improve image quality in all three dimensions.

The next step in the invented method is to view the data set from the projection plane 60. As shown in FIG. 4, the projection plane 60 is perpendicular to the slices of data. Each horizontal line 63 of the projected image which is to be displayed is formed from a single slice of data. The projection process is, therefore, applied iteratively to each slice of data to produce sixty-three horizontal lines 63 in the image. The projection of each slice of data onto a line 63 in the image is a two-dimensional process which is shown best in FIG. 6.

Figure 6:
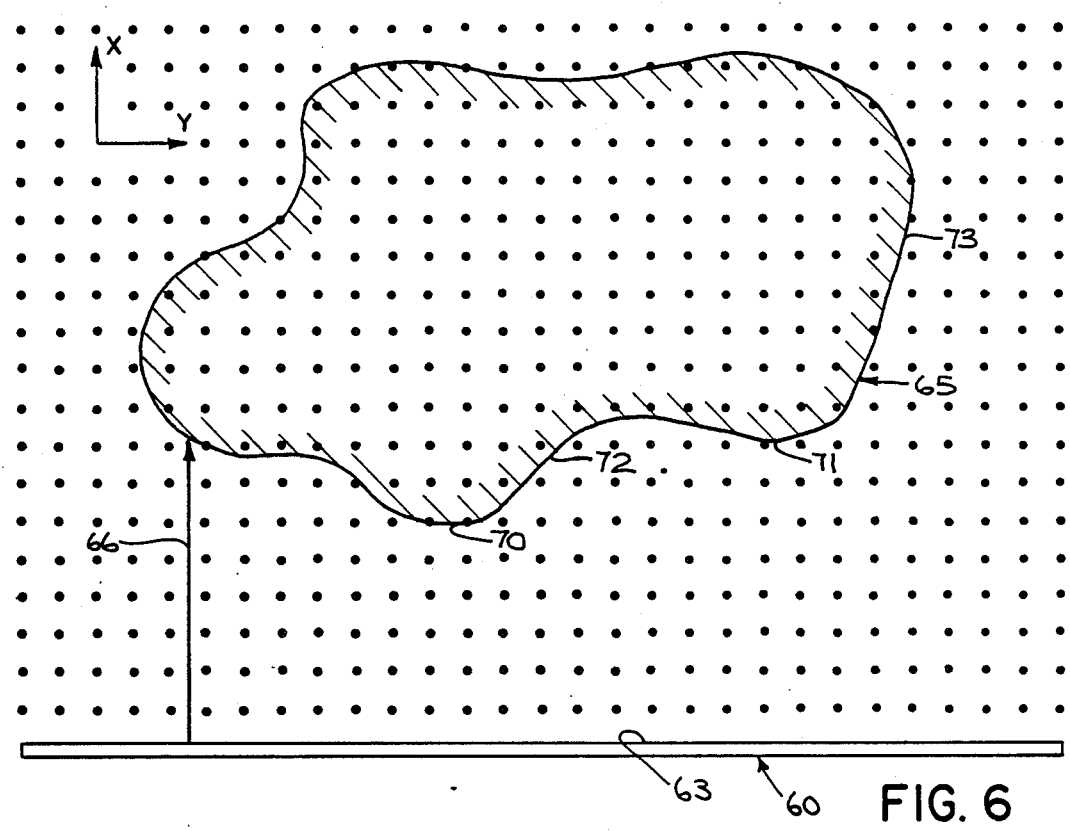
FIGS. 6 and 7 are pictoral representations of another step in the method of the present invention.

Referring now to FIG. 6, the projection process will first be described in general terms. The slice of data is a two-dimensional array of data points v(x,y). Each data point indicates the number of nuclear events in its surrounding volume, or voxel. Those data points which lie within the boundary 65 of the object to be imaged will have values that exceed a preselected threshold value. To find the boundary 65, therefore, the data points are methodically examined beginning with those closest to the projection plane 60 and extending away therefrom. When a data point is found that exceeds the threshold, the boundary is located. As will be described in more detail below, shading values are then calculated for each pixel in the line 63 which is a function of the distance between that pixel and the located boundary. If no boundary is found, a back-ground value is assigned to the corresponding pixel.

Figure 7:
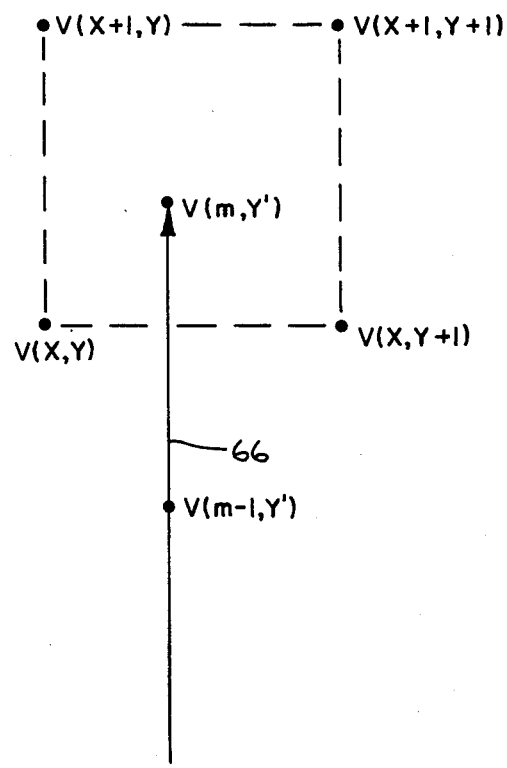

Referring still to FIG. 6, the shading of each pixel in the image line 63 is determined by a process of extending a projector 66 from the pixel, away from the projection plane 60 along the x axis. This projection process is an iterative process in which the projector is advanced an increment (for example 6.4 millimeters) in the x direction and the value of the data at the new location is determined. This process continues until the projector is extended into a region where the calculated nuclear event count value exceeds the predetermined threshold value. The count value V(m) at each such iteration is calculated by bilinear interpolation between the four surrounding data points in the slice as illustrated in FIG. 7.

$$V(m,y') = V(x,y)*(1 - dx)*(1 - dy) + \\ V(x + 1,y)*(dx)*(1 - dy) + \\ V(x + 1,y + 1)*(dx)*(dy) + \\ V(x,y + 1)*(1 - dx)*(dy)$$ (2)

where:

$dx = X_m - x$ $dy = Y_m - y$ $X_m$, $Y_m$ = location of the projector for the current iteration-floating point values x,y = integer location values of the projector.

When the count value V(m) exceeds the threshold, the boundary has been crossed. To increase the resolution of the image along the distance, or x direction, however, the current location of the projector alone is not used to set the pixel shading. Instead, as indicated by the following expression, the previous location is also used.

Projector Distance = $D(m) - STEP[(V(m) - Threshold)/(V(m) - V(m-1))]$ (3)

where:

D(m) = distance to current location
STEP = increment of distance between iterations (6.4 mm)
V(m) = current count value
V(m−1) = count value of previous iteration Thus, instead of measuring the distance to the object in whole 6.4 millimeter steps, or increments, the exact distance is determined by linearly interpolating between the current projector location and the projector location during the previous iteration using the nuclear event counts at each respective location. This enables a high resolution along the x coordinate to be achieved without using very small steps, or increments, in the projector advance. As a result, the projector 66 is advanced more quickly with a resulting reduction in processing time. When the processing has been completed for all pixels in the projection plane 60, a two-dimensional array of distance data D(z,y) is stored in the disk recorder 39.

Each projector distance value in the distance array D(z,y) is then subtracted from a constant value to produce a shading value for its pixel. Thus, the longer the projector distance, the darker the pixel shading is set. If a projector does not intersect the object of interest, the pixel is set to a background shade. This process is repeated for each pixel in the line 63 (i.e. along the y axis) to produce a subset of data which indicates the brightness of a single line in the image. The process is then repeated for each line 63 in the image (i.e. along the z axis) to produce an image array DS(z,y) which describes the entire three-dimensional image of the object of interest. The shading of this image is solely determined by distance from the projection plane 60, with more distant surfaces appearing darker. Such shading does not, however, account for the angle of the surface of the object with respect to the observer and the light source.

To further enhance the three-dimensional image embodied in the display array DS(z,y), the pixel shading is further modified to highlight features on the surface of the object. This is accomplished using a unique gradient shading method which will now be described.

Referring particularly to FIG. 6, when the object 65 is viewed from the projection plane 60, those points on its surface, which directly face the projection plane 60 should appear brighter than those which are at a sharp angle. For example, the points 70 and 71 on the object 65 directly face the projection plane 60, whereas the points 72 and 73 lie on surfaces which are at an angle. The method of the present invention calculates the gradient of each point on the object 65 which faces the projection plane 60, and further modifies the "distance-shaded" image by darkening points on the surface as a function of gradient. The resulting 3-D image is accentuated as if the object were illuminated by a light source behind the observer. In addition, as will be explained in detail below, the radiologist can control the magnitude of this gradient-shading accentuation to produce a variety of images.

The gradient values (GR) are calculated using the array of distance image values DS(z,y) which were calculated as described above. This array of data is illustrated graphically in FIG. 8 in which the projection plane 60 is now parallel to the plane of the drawing. At points on the object 65 where the distance image values DS(z,y) remain constant in both the z and y direction, the object's surface is parallel to the projection plane 60 and its gradient is thus zero. At points where the distance image values DS(z,y) are different along either the z axis, the y axis or both, the gradient value will have a positive value. To calculate these gradient values a 2 × 2 operator is employed to process the distance image array DS(z,y) in accordance with the following expression:

$$A = DS(z+1, y+1) - DS(z,y) \quad (4)$$
$$B = DS(z+1,y) - DS(z, y+1)$$
$$GR(u,v) = \sqrt{A^2 + B^2}$$

Figure 8:
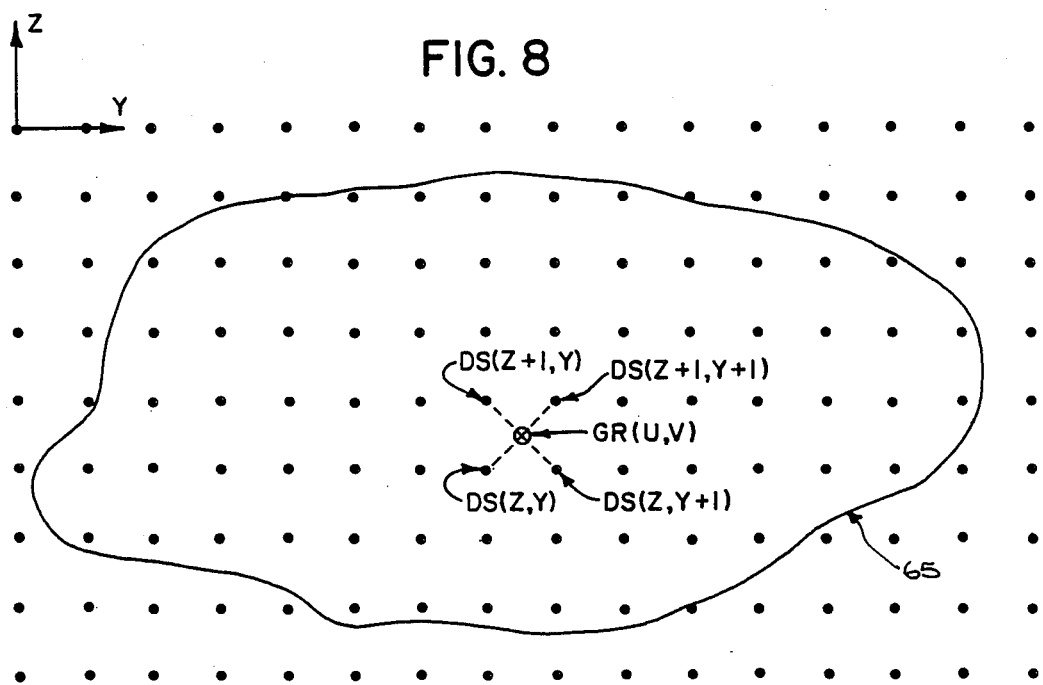
FIG. 8 is a pictoral representation of yet another step in the method of the present invention.

As shown in FIG. 8, the values A and B are differences across the respective diagonals of each 2 × 2 kernal, with the result that the gradient value GR(u,v) is the gradient at the center of the kernal, where:

$u = z + 0.5$
$v = y + 0.5$

The 2 × 2 operator is thus applied to each 2 × 2 set of distance values in the array DS(z,y) to produce a corresponding array of gradient values GR(u,v). It should be obvious to those skilled in the art that the same result can be achieved by using the distance array D(z,y) rather than the distance image array DS(z,y). In either case, the resulting gradient values have a finer resolution than when the more conventional 3 × 3 operator is used to make the gradient calculations. As a result of using the 2 × 2 operator, however, is that the position of the gradient values is offset one-half pixel in each dimension from its corresponding distance image value in the array DS(z,y).

Before the gradient values GR(u,v) can be added to the display image values DS(z,y), the display values are translated one half pixel in both the z and y directions so that the points in the array correspond to the points in the gradient array GR(u,v). This translation is performed by the following linear interpolation expression:

$$DS(u,v) = [DS(z,y) + DS(z+1,y) + DS(z+1,y+1) + DS(z,y+1)]/4 \quad (5)$$

The final 3-D image is produced by adding the gradient values to the display array in accordance with the following expression:

$$CS(u,v) = DS(u,v) + ZMAG/(1 + k*GR(u,v))$$

where:

ZMAG = the magnitude to be added to the distance number when the gradient is zero (i.e. a plane facing the observer)

K = a constant which may be adjusted by the radiologist to control the degree of gradient shading.

Referring again to FIG. 2, the array CS(u,v) is stored in the disk recorder 39 and it may be read out to the display controller 42 to produce a shaded 3-D image on the CRT display 43. The last step in the processing indicated by equation (6) above is quickly performed by the CPU 38. As a result, the radiologist can easily and quickly produce an entire set of shaded images in which the amount of gradient shading in each is different.

It should be apparent to those skilled in the art that many variations are possible from the preferred embodiment of the invention described herein. For example, the coordinate system and the orientation of the slices and the projection plane within that coordinate system can differ. Also, the number of pixels in the volume of interest and the number of lines in the image to be displayed can differ from that described herein.

I claim:

1. A method for producing a shaded image from data acquired with a nuclear imaging tomographic scanner, the steps comprising:
   (a) acquiring a sequence of two-dimensional frames of nuclear event data which is reconstructed to form a three-dimensional array of data V(x,y,z) which indicates the number of nuclear events at a three-dimensional matrix of points throughout a volume of interest;
   (b) extending into the volume of interest a projector from a pixel in a projection plane to determine the distance between that pixel in the projection plane and the boundary of an object within the volume of interest, including the steps of:
      (i) extending the projector an incremental distance away from the projection plane,
      (ii) calculating the number of nuclear events at the current position of the projector from the three-dimensional array of data, V(x,y,z),
      (iii) comparing the calculated number of nuclear events with a pre-established threshold value,
      (iv) reiterating steps i–iii if the threshold value is not reached, otherwise,
      (v) calculating the location at which the projector intersects the object's boundary by interpolating between the current calculated number of nuclear events and the calculated number of nuclear events from the previous iteration to arrive at a location between the projector's current position and its position for the previous iteration;
   (c) producing a two-dimensional array of distance data D(z,y) by repeating step (b) for each pixel in the projection plane; and
   (d) producing a two-dimensional display data array DS(z,y) by assigning a brightness value to each element in the display data array which is a function of the distance value of its corresponding element in the distance array D(z,y).

2. The method as recited in claim 1 in which the nuclear event data is a series of two-dimensional frames V(x,y) which are spaced apart along one axis (z), and the three-dimensional array of data V(x,y,z) is formed by interpolating between corresponding points in adjacent frames.

3. The method as recited in claim 1 in which the value of each brightness element in the display data array DS(z,y) is modified y the value of a corresponding element in a gradient array and the gradient array is produced by calculating the gradient of the object's surface at points adjacent to each intersection of a projector and the boundary of the object.

4. The method as recited in claim 3 in which each successive gradient array element is calculated by applying a 2 × 2 operator to each successive 2 × 2 set of elements in the display data array DS(z,y).

5. The method as recited in claim 4 in which the elements of the display data array DS(z,y) are modified to represent the brightness values of corresponding pixel elements DS(u,v) which have been shifted one-half pixel distance away along each of the two dimensions (z and y).

6. The method as recited in claim 5 in which the elements of the modified display array DS(u,v) are further modified by adding a value to each which is calculated using a corresponding element in the gradient array.

* * * * *